United States Patent
Nygren

(10) Patent No.: US 8,996,129 B2
(45) Date of Patent: Mar. 31, 2015

(54) MEDICAL ELECTRODE INCLUDING AN IRIDIUM OXIDE SURFACE AND METHODS OF FABRICATION

(75) Inventor: Lea A Nygren, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 1082 days.

(21) Appl. No.: 11/669,512

(22) Filed: Jan. 31, 2007

(65) Prior Publication Data

US 2008/0183260 A1  Jul. 31, 2008

(51) Int. Cl.
| | |
|---|---|
| *A61N 1/05* | (2006.01) |
| *A61B 5/042* | (2006.01) |
| *C23C 14/00* | (2006.01) |
| *C23C 14/02* | (2006.01) |
| *C23C 14/08* | (2006.01) |

(52) U.S. Cl.
CPC . *A61N 1/05* (2013.01); *A61B 5/042* (2013.01); *A61N 1/056* (2013.01); *C23C 14/0036* (2013.01); *C23C 14/028* (2013.01); *C23C 14/085* (2013.01); *A61B 2562/125* (2013.01)
USPC ............ 607/116; 600/377; 607/119

(58) Field of Classification Search
USPC .......... 600/372, 373, 377; 607/115, 116, 121, 607/122, 141
See application file for complete search history.

(56) References Cited

U.S. PATENT DOCUMENTS

| | | |
|---|---|---|
| 3,975,557 A | 8/1976 | Kuchek |
| 4,280,514 A | 7/1981 | MacGregor |
| 4,502,492 A | 3/1985 | Bornzin |
| 4,506,680 A | 3/1985 | Stokes |
| 4,649,937 A | 3/1987 | DeHaan et al. |
| 4,677,989 A | 7/1987 | Robblee |
| 4,679,572 A | 7/1987 | Baker, Jr. |
| 4,717,581 A | 1/1988 | Robblee |
| 4,735,205 A | 4/1988 | Chachques et al. |
| 4,762,136 A | 8/1988 | Baker |

(Continued)

FOREIGN PATENT DOCUMENTS

| | | |
|---|---|---|
| EP | 237316 A2 | 10/1987 |
| EP | 237316 A3 | 5/1988 |

(Continued)

OTHER PUBLICATIONS

E. Slavcheva, R. Vitushinsky, W. Mokwa and U. Schnakenberg, Sputtered Iridium Oxide Films as Charge Injection Material for Functional Electrostimulation, 2004, Journal of Electrochemical Society, 151 (7), E226-E236.*

(Continued)

*Primary Examiner* — Carl H Layno
*Assistant Examiner* — Jennifer Ghand
(74) *Attorney, Agent, or Firm* — Mueting, Raasch & Gebhardt, P.A.

(57) ABSTRACT

An implantable medical electrode includes a substrate and an iridium oxide surface, which is formed by an iridium oxide film applied over a roughened surface of the substrate. The film is preferably applied via direct current magnetron sputtering in a sputtering atmosphere comprising argon and oxygen. A sputtering target power may be between approximately 80 watts and approximately 300 watts, and a total sputtering pressure may be between approximately 9 millitorr and approximately 20 millitorr. The iridium oxide film may have a thickness greater than or equal to approximately 15,000 angstroms and have a microstructure exhibiting a columnar growth pattern.

27 Claims, 8 Drawing Sheets

(56) References Cited

U.S. PATENT DOCUMENTS

| | | | |
|---|---|---|---|
| 4,784,160 A | | 11/1988 | Szilagyi |
| 4,860,446 A | * | 8/1989 | Lessar et al. ................... 29/858 |
| 4,919,135 A | | 4/1990 | Phillips, Jr. et al. |
| 4,934,049 A | | 6/1990 | Kiekhafer et al. |
| 5,016,645 A | | 5/1991 | Williams et al. |
| 5,074,313 A | | 12/1991 | Dahl et al. |
| 5,097,843 A | | 3/1992 | Soukup et al. |
| 5,181,526 A | | 1/1993 | Yamasaki |
| 5,265,608 A | | 11/1993 | Lee et al. |
| 5,282,844 A | | 2/1994 | Stokes et al. |
| 5,314,458 A | | 5/1994 | Najafi et al. |
| 5,318,572 A | | 6/1994 | Helland et al. |
| 5,326,448 A | | 7/1994 | Otten |
| 5,360,442 A | | 11/1994 | Dahl et al. |
| 5,397,343 A | | 3/1995 | Smits |
| 5,534,022 A | | 7/1996 | Hoffmann et al. |
| 5,545,207 A | | 8/1996 | Smits et al. |
| 5,571,158 A | | 11/1996 | Bolz et al. |
| 5,587,200 A | | 12/1996 | Lorenz et al. |
| 5,654,030 A | | 8/1997 | Munshi et al. |
| 5,683,443 A | | 11/1997 | Munshi et al. |
| 5,985,368 A | | 11/1999 | Sangeeta et al. |
| 6,224,985 B1 | | 5/2001 | Shah et al. |
| 6,253,110 B1 | | 6/2001 | Brabec et al. |
| 6,430,447 B1 | | 8/2002 | Chitre et al. |
| 6,430,448 B1 | | 8/2002 | Chitre et al. |
| 6,931,286 B2 | | 8/2005 | Sigg et al. |
| 7,022,621 B1 | | 4/2006 | Zhang et al. |
| 7,053,403 B1 | | 5/2006 | Zhang et al. |
| 7,098,144 B2 | | 8/2006 | Zhang et al. |
| 7,194,315 B1 | | 3/2007 | Platt et al. |
| 2001/0032005 A1 | | 10/2001 | Gelb et al. |
| 2002/0081243 A1 | | 6/2002 | He |
| 2004/0086542 A1 | * | 5/2004 | Hossainy et al. ............ 424/423 |
| 2004/0111141 A1 | | 6/2004 | Brabec et al. |
| 2004/0176828 A1 | | 9/2004 | O'Brien |
| 2004/0220652 A1 | | 11/2004 | Zhou et al. |
| 2004/0240152 A1 | | 12/2004 | Schott et al. |
| 2005/0048876 A1 | | 3/2005 | West et al. |
| 2005/0049665 A1 | | 3/2005 | Brabec et al. |
| 2005/0057136 A1 | * | 3/2005 | Moriya et al. ................ 313/311 |
| 2005/0131509 A1 | | 6/2005 | Atanassoska et al. |
| 2005/0183952 A1 | * | 8/2005 | Shimamune et al. .... 204/290.01 |
| 2005/0238686 A1 | * | 10/2005 | Hossainy et al. ............. 424/423 |
| 2005/0246002 A1 | | 11/2005 | Martinez |
| 2006/0086314 A1 | | 4/2006 | Zhang et al. |
| 2006/0160304 A1 | | 7/2006 | Hsu et al. |
| 2006/0167536 A1 | | 7/2006 | Nygren et al. |
| 2006/0259109 A1 | | 11/2006 | Zhou et al. |
| 2007/0179374 A1 | * | 8/2007 | Nygren et al. ................. 600/372 |
| 2007/0265692 A1 | * | 11/2007 | Koop et al. .................... 607/119 |
| 2008/0253922 A1 | | 10/2008 | Trimmer et al. |
| 2010/0084266 A1 | | 4/2010 | Di Franco |
| 2010/0137963 A1 | | 6/2010 | Nygren et al. |

FOREIGN PATENT DOCUMENTS

| | | |
|---|---|---|
| EP | 237316 B1 | 8/1993 |
| WO | WO 02/32497 A1 | 4/2002 |
| WO | WO 2004/073790 A1 | 9/2004 |
| WO | WO/2006081344 A1 | 8/2006 |

OTHER PUBLICATIONS

C.U. Pinnow, I. Kasko, C. Dehm, B. Jobst, M. Seibt and U. Geyer, Preparation and properties of dc-sputtered IrO2 and Ir thin films for oxygen barrier applications in advanced memory technology, 2001, Journal of Vacuum Science and Technology, 19 (5), 1857-1865.*

U.S. Supplemental Search Results, U.S. Appl. No. 11/669,512, filed Jan. 30, 2008, 5 Pages.

Weiland, James D., et al., "Chronic Neural Stimulation with Thin-Film, Iridium Oxide Electrodes", IEEE: Transactions of Biomedical Engineering, vol. 47, No. 7, Jul. 2000.

Ison et al., "Platinum and platinum/iridium electrode properties when used for extracochlear electrical stimulation of the totally deaf," *Medical and Biological Engineering & Computing*, 1987; 25(4):403-413.

Barrett et al., "The Principles of Engineering Materials," Prentice-Hall, Inc., Englewood Cliffs, NJ, 1973; title pages and pp. 36-37.

* cited by examiner

MEDICAL ELECTRODE INCLUDING AN IRIDIUM OXIDE SURFACE AND METHODS OF FABRICATION

TECHNICAL FIELD

The present invention pertains to implantable medical electrodes and more particularly to implantable medical electrodes having iridium oxide surfaces.

BACKGROUND

Medical electrodes having surfaces of enhanced microstructure (i.e. an increased active surface area), in order to increase a capacitance of the electrode-to-tissue interface, thereby reducing post-pulse polarization, particularly for cardiac pacing and sensing applications, are well documented in the art. For example, coatings or layers of platinum black particles, titanium nitride (TiN) and iridium oxide (IrOx), which extend over electrode substrates to create the enhanced microstructure, have been described, along with methods for applying these layers. However, there is still a need for new processes/methods to create electrode surfaces of enhanced microstructure. The new processes can improve production efficiency and can lead to further increases in active surface area by means of corresponding process-dependent surface microstructure features.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1:
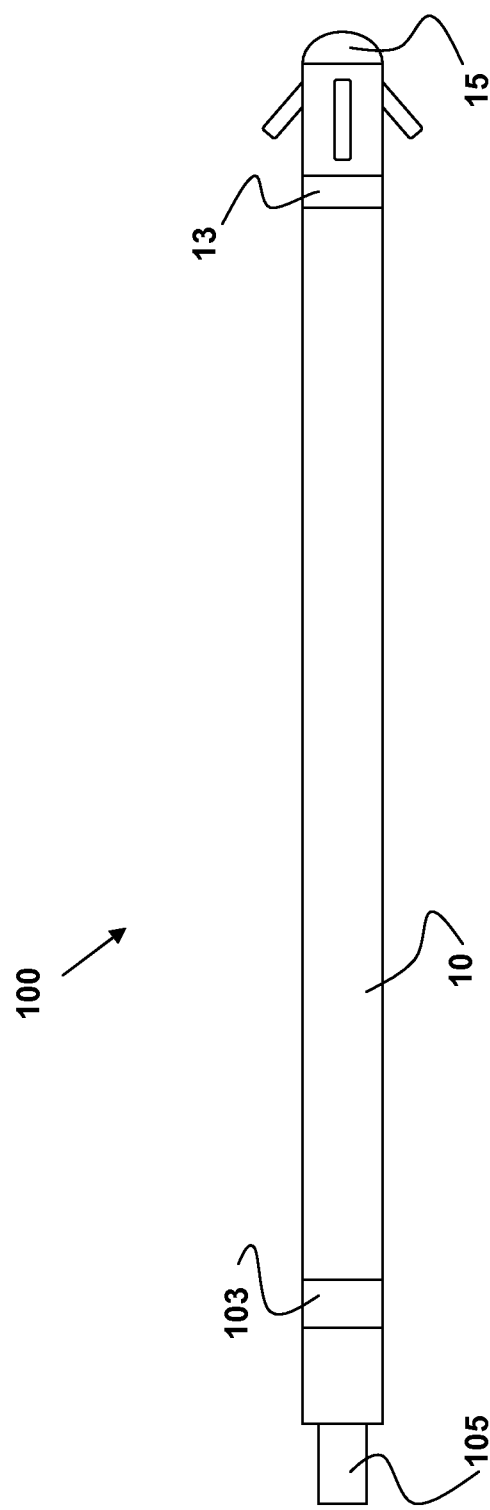
FIG. 1 is a plan view of an exemplary medical electrical lead including electrodes which may be fabricated according to methods of the present invention.

FIG. 1 is a plan view of an exemplary medical electrical lead 100 including electrodes 13, 15, which may be fabricated according to methods of the present invention. FIG. 1 illustrates lead 100 including an elongate insulative body 10 terminated at a distal end by tip electrode 15, and at a proximal end by a connector pin 105, which is coupled to tip electrode 15 by a conductor (not shown) extending within body 10. FIG. 1 further illustrates electrode ring 13 mounted to body 10, in proximity to tip electrode 15, and a connector ring 103, which mounted to body 10 in proximity to connector pin 105, and is coupled to electrode ring 13 by another conductor (not shown) extending within body 10. Lead 100 is an exemplary bipolar pacing lead, wherein tip electrode 15 is disposed to contact tissue for the application of stimulation pulses, and, in conjunction with electrode ring 13, to sense electrical activity of the tissue; the construction and application of medical electrical leads like lead 100 are well known to those skilled in the art. Either or both of electrodes 13, 15 may include a surface of enhanced microstructure formed according to methods of the present invention, however the sensing function of electrodes 13 and 15, together (bipolar), or of electrode 15 in a unipolar mode, may particularly benefit from tip electrode 15 having such a surface.

Those skilled in the art understand that a polarization of tip electrode 15 following the delivery of pacing pulses can impact sensing of an evoked response of the tissue to the pacing pulse. Thus, an increased active surface area of electrode 15, provided by an enhanced microstructure of the surface, formed according to methods of the present invention, is desirable for increasing a capacitance of the tissue interface with electrode 15 to a level that sufficiently reduces post-pulse polarization voltages, so that evoked response signals are not 'masked' by these polarization voltages and can be sensed.

According to embodiments of the present invention, electrodes, such as electrode 15, include an IrOx surface formed by reactively sputtering a layer, or film of IrOx over an electrode substrate, for example, formed from titanium or a platinum/iridium (Pt/Ir) alloy. Methods of the present invention employ DC magnetron sputtering; preferred sputtering process parameters were established by varying the parameters in a designed experiment using titanium foils as the substrate. The processing parameters which were varied were: sputtering target power: from approximately 100 watts to approximately 300 watts; total sputtering pressure: from approximately 9 millitorr to approximately 15 millitorr; and a composition of the sputtering atmosphere: from approximately 25% oxygen/argon ratio to approximately 75% oxygen/argon ratio. Samples of each group corresponding to each combination of process parameters were subjected to electrical performance evaluations, which included measurements of capacitance and impedance as a function of frequency (0.1 Hz-1000 Hz). The processing parameters, which are presented in Table 1, resulted in the highest capacitance at the lowest frequency and were subsequently used to sputter IrOx films onto electrode substrates, for which polarization and impedance measurements were made.

TABLE 1

| Target power (watts) | ~100 |
|---|---|
| Total pressure (millitorr) | ~15 |
| Oxygen/Argon (%) | ~75 |

Figure 2:
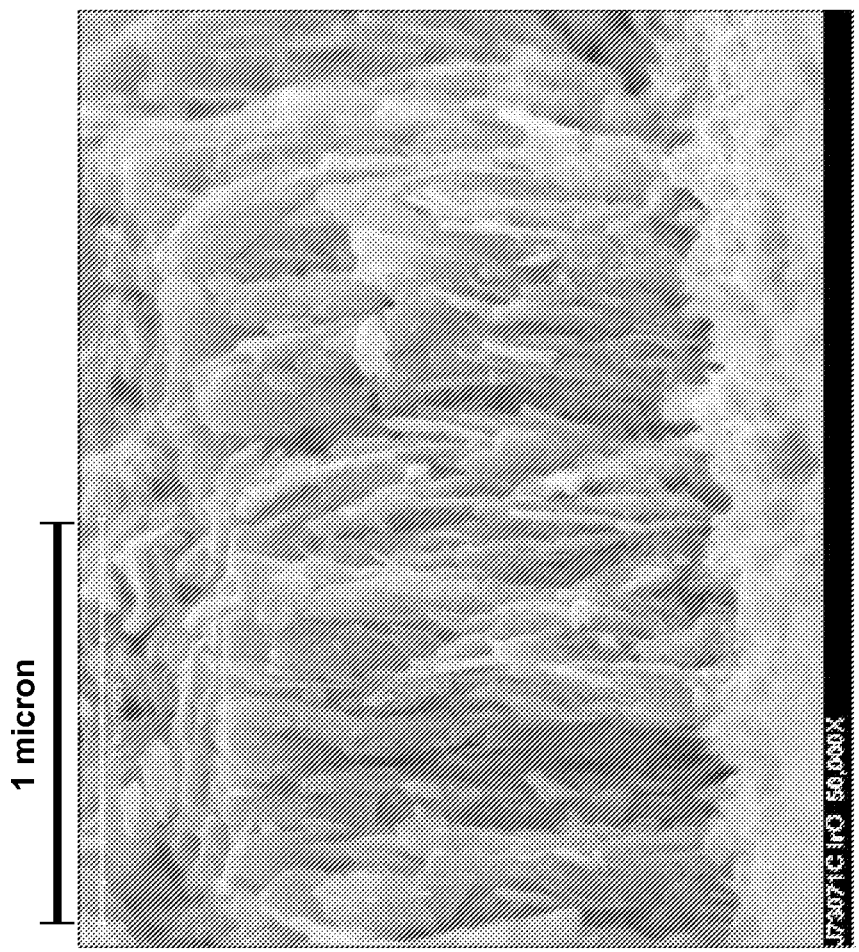
FIG. 2 is a scanning electron microscope (SEM) photograph, taken at a magnification of 50,000×, of a cross-section of an exemplary IrOx film formed by applying an IrOx film according to a sputtering method of the present invention.

IrOx films were sputtered, according to the above process parameters, onto Pt/Ir electrode substrates whose surfaces had been mechanically abraded by grit blasting with a 50-micron alumina powder; prior to sputtering the electrodes were cleaned in an ultrasonic bath of acetone and IPA for approximately 5 minutes, and then blown dry. The electrodes were hemispherical in form, similar to electrode 15 shown in FIG. 1, having a diameter of approximately 0.068 inch. One group, Group A, of the electrodes was sputtered for a period time to achieve a film thickness of approximately 15,000 angstroms, and another group of the electrodes, Group B, for a shorter period of time to achieve a thickness of approximately 4,500 angstroms. A deposition rate of the process, according to the above parameters, had been determined by placing standard sapphire thickness monitors in the sputtering chamber with the titanium foils and then measuring resulting IrOx film thicknesses with a Dektak profilometer for various sputtering times. FIG. 2 is a SEM photograph, taken at a magnification of 50,000×, of a cross-section of an IrOx film, formed over a sapphire thickness monitor, according to the above parameters and for a time to achieve a thickness of approximately 15,000 angstroms, which corresponds to the thickness for Group A electrodes. With reference to FIG. 2, it may be appreciated that the IrOx film creates a surface having a microstructure exhibiting a columnar growth pattern.

Figures 3A, 3B:
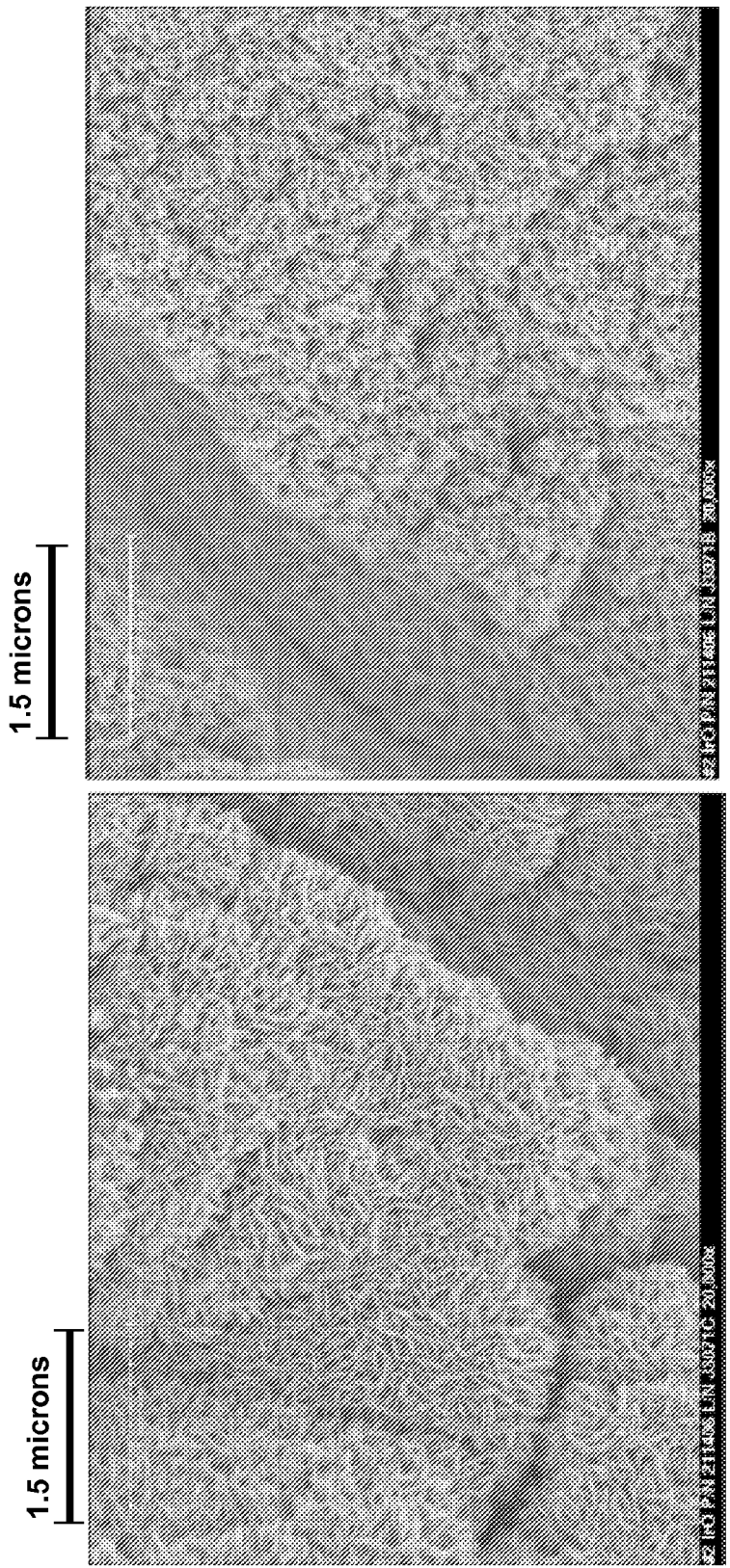
FIGS. 3A-B are SEM photographs, taken at a magnification of 20,000×, of exemplary electrode surfaces formed by application methods of the present invention.
Figure 4:
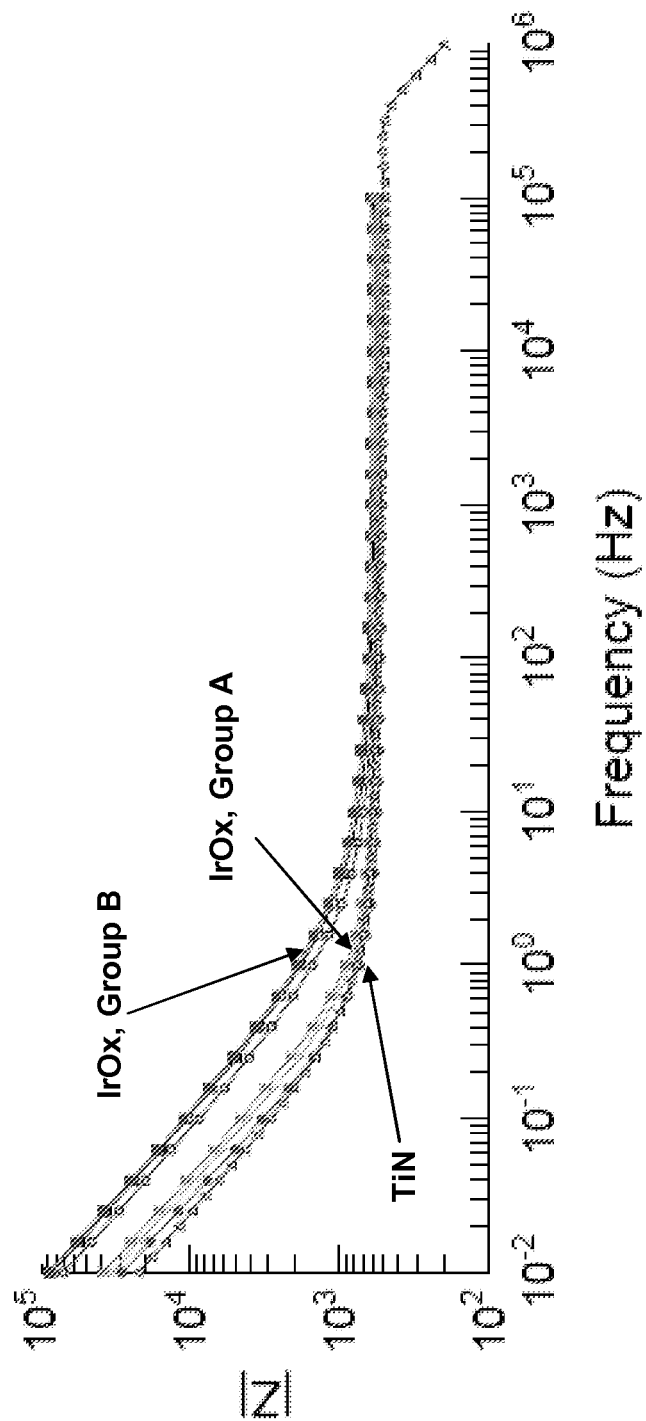
FIG. 4 is a plot of impedance versus frequency characterizing exemplary electrodes of the present invention.

FIGS. 3A-B are SEM photographs, taken at a magnification of 20,000×, of electrode surfaces for Group A and Group B electrodes, respectively. With reference to FIGS. 3A-B it may be appreciated that the surface created by the thicker IrOx film of Group A electrodes (FIG. 3A) exhibits longer columnar features than that created by the thinner IrOx film of Group B electrodes (FIG. 3B), which may result in a greater active surface area. Results of electrical performance evaluations for the two groups provide some evidence of a greater active surface area for Group A electrodes. Unipolar polarization voltages were measured 20 msec post-pulse (pulse of 4V over 1 ms) for electrodes from Groups A and B, which had been built into leads and soaked in a saline tank for approximately 24 hours; those of Group A, having the thicker IrOx film forming the surface thereof, demonstrated lower polarization than those in Group B: 3.9 mV, on average, for Group A electrodes, versus 7.1 mV, on average, for Group B electrodes (n=3). The Group A polarization is comparable to that of a standard electrode having a hemispherical form of similar gross dimension and a TiN surface (approximately 3 mV), and, with reference to FIG. 4, it may be appreciated that impedance as a function of frequency for the Group A electrodes closely matches that for the electrodes having the TiN surface. In particular, it is important to note that the impedance at 1 Hz, which is the order of magnitude for pacing pulse frequency, does not significantly rise for the Group A electrodes from that measured at the higher frequencies. The impedances were estimated via sampling current, 10 times, per decade of frequency, in response to an applied 10 mV AC voltage.

The mechanical stability of the IrOx films on electrodes of Groups A and B were also tested by stressing the films via cyclic voltammetry. Films of both groups remained adhered during cyclic loading of ±1V at a rate of ±10 mV/sec, and upon being impinged with a 'blast' of saline from a syringe following the cyclic voltammetry.

Figure 5A:
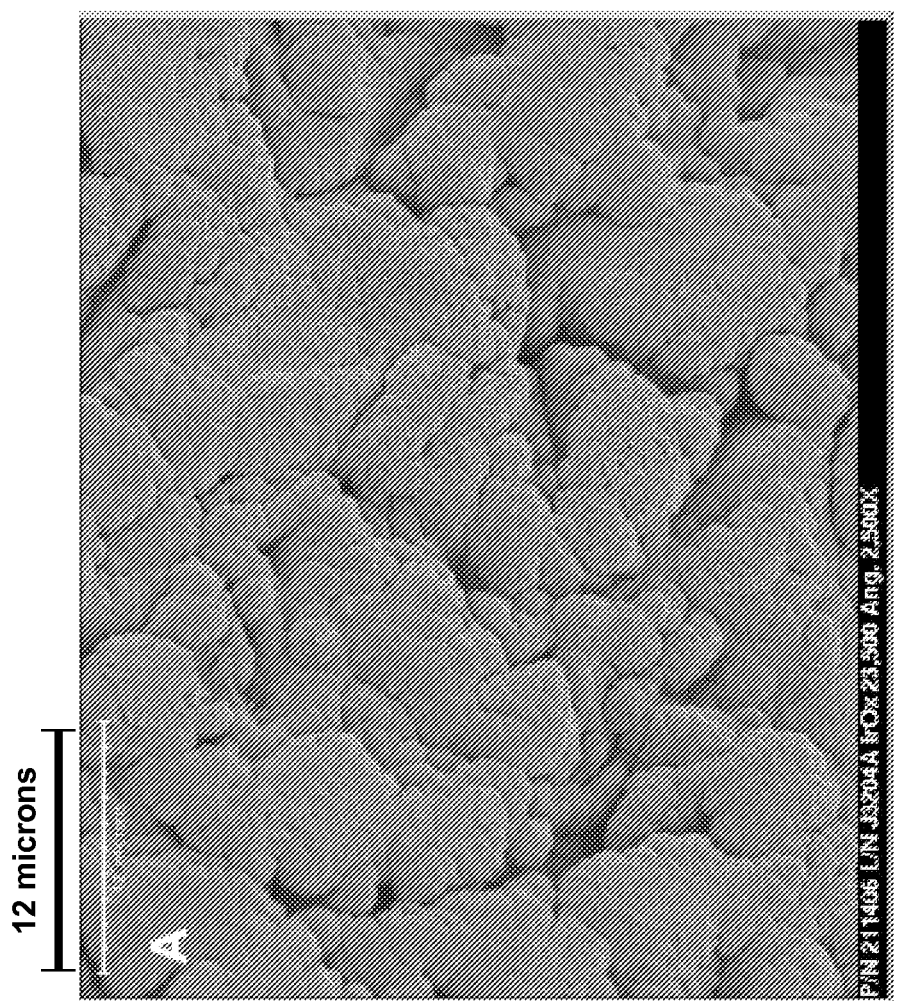
FIGS. 5A-B are SEM photographs, taken at magnifications of 2,500× and 20,000×, respectively, of an electrode surface formed by a sputtered IrOx film, according to some embodiments of the present invention.
Figure 5B:
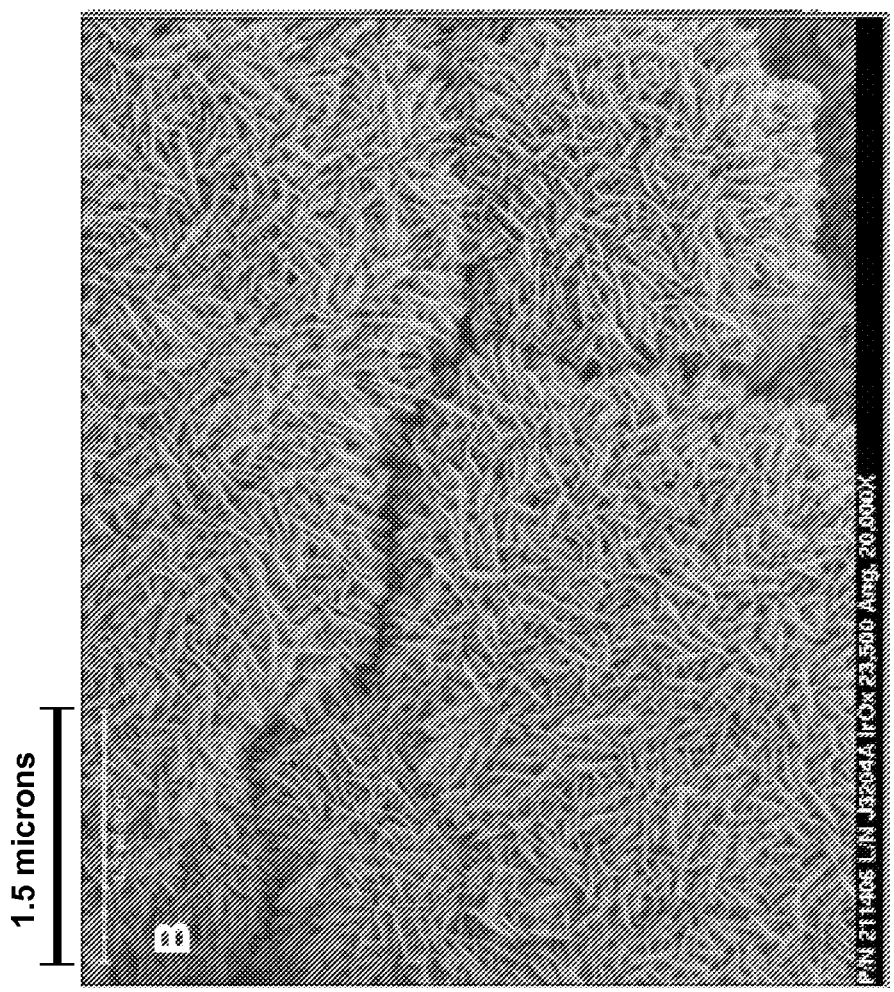

FIGS. 5A-B are SEM photographs, taken at magnifications of 2,500× and 20,000×, respectively, of an exemplary electrode surface formed by a thicker sputtered IrOx film than that of the Group A electrodes. The electrode surface shown in FIGS. 5A-B was achieved by DC magnetron sputtering according to the process parameters presented in Table 1. As for the substrates of Groups A and B, the Pt/Ir substrates of electrodes corresponding to FIGS. 5A-B were mechanically abraded via grit blasting with a 50-micron alumina powder prior to sputtering, but a thicker film of IrOx, approximately 23,500 angstroms thick, was sputtered onto the FIGS. 5A-B electrodes. It was expected that the thicker film would result in an increased active surface area, and an average post-pulse polarization voltage of the electrodes corresponding to FIGS. 5A-B was indeed measured to be lower than that of Group A electrodes: 2.6 mV versus the 3.9 mv of Group A electrodes. (As with Group A and B electrodes, unipolar polarization voltages were measured 20 msec post-pulse (pulse of 4V over 1 msec) for the electrodes of FIGS. 5A-B, which were built into a lead and soaked in a saline tank for approximately 24 hours.) The electrodes corresponding to FIGS. 5A-B demonstrated similar frequency-dependent impedance to that described for Group A electrodes.

Figure 6A:
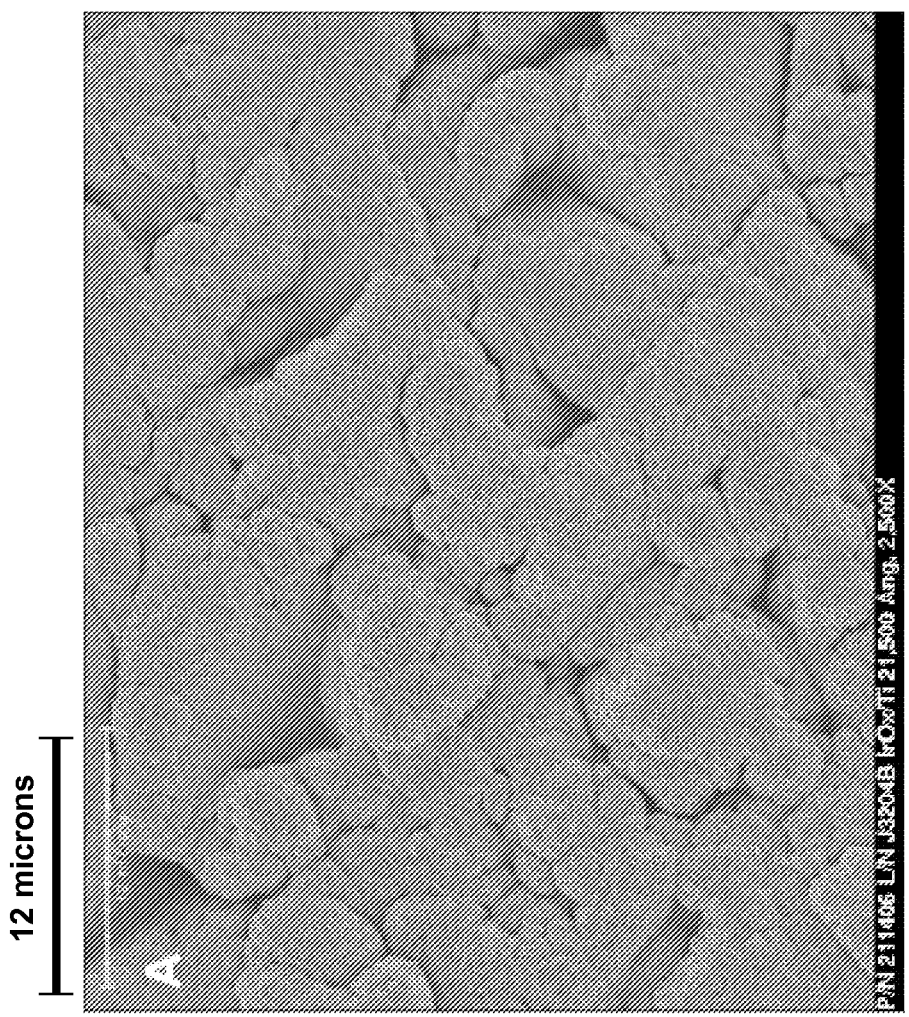
FIGS. 6A-B are SEM photographs, taken at magnifications of 2,500× and 20,000×, respectively, of an electrode surface formed by a sputtered IrOx film, according to additional embodiments of the present invention.
Figure 6B:
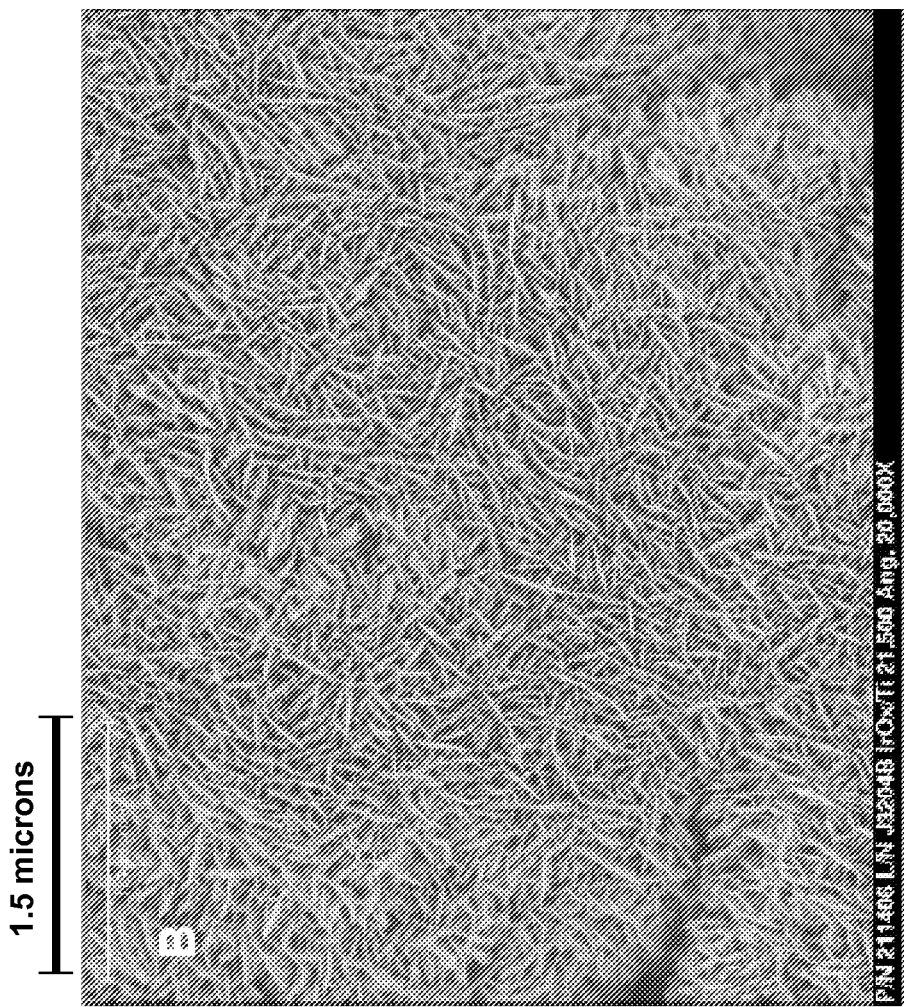

FIGS. 6A-B are SEM photographs, taken at magnifications of 2,500× and 20,000×, respectively, of an exemplary electrode surface of an alternate embodiment formed by a IrOx film sputtered over a layer of titanium covering a Pt/Ir electrode substrate. The layer of titanium was applied by DC magnetron sputtering in an argon/oxygen environment, wherein the sputtering target power was approximately 200 watts and the argon pressure approximately 11.5 millitorr; those skilled in the art will appreciate that other suitable process parameters may be employed to apply the titanium layer. The illustrated IrOx film is thicker than that of the Group A electrodes, being approximately 21,500 angstroms thick, and was formed by DC magnetron sputtering according to the process parameters presented in Table 1. With reference back to FIG. 5B, in conjunction with FIG. 6B, it should be appreciated that the microstructure of the surface created by the IrOx film sputtered directly over the electrode substrate (FIG. 5B) is very similar to that created by the film sputtered over the interposing layer of titanium (FIG. 6B). Furthermore, electrodes having IrOx surfaces corresponding to FIGS. 6A-B demonstrated similar polarization and frequency-dependent impedance to that of the electrodes having IrOx surfaces corresponding to FIGS. 5A-B, but the layer of titanium interposed between the Pt/Ir substrate and the IrOx film enhanced the mechanical stability, or adhesion to the substrate, of the film shown in FIGS. 6A-B over that shown in FIGS. 5A-B. It should be noted that other materials, for example, iridium, niobium or zirconium, may be substituted for titanium, as an interposing layer to enhance the mechanical stability of the IrOx film, without significantly altering the character of the surface microstructure created by the IrOx film from that shown in FIGS. 5B and 6B, or the resulting electrical properties.

A DC magnetron sputtering deposition rate for applying IrOx to an electrode surface, which is between approximately 100 angstroms per minute and approximately 2500 angstroms per minute, according to the processing methods previously defined, can be one or two orders of magnitude greater than that for applying TiN. Thus, the performance of electrodes including the IrOx film(s), according to the results presented herein, demonstrate that a sputtered IrOx electrode surface, formed according to process parameters of the present invention, is a viable alternative to a TiN surface, and may provide a benefit by increasing production efficiency via increased sputtering deposition rates. Finally, it should be noted that the preferred processing parameters described above may vary for different electrode geometries and sputtering system configurations without significantly altering the surface microstructure created by the sputtered IrOx films from that of those presented herein.

In the foregoing detailed description, the invention has been described with reference to specific embodiments. However, it may be appreciated that various modifications and changes can be made without departing from the scope of the invention as set forth in the appended claims.

I claim:

1. A method for fabricating an implantable medical electrode, the method comprising:
mechanically roughening a surface of a substrate; and
applying a film of iridium oxide over the roughened surface using direct current magnetron sputtering in a sputtering atmosphere comprising oxygen and argon, wherein a sputtering deposition rate is between approximately 100 angstroms/minute and approximately 2500 angstroms/minute, and wherein the film has a microstructure exhibiting a columnar growth pattern.

2. The method of claim 1, wherein mechanically roughening the surface comprises grit blasting with particles having approximately 50 micron diameters.

3. The method of claim 1, wherein a ratio of the oxygen to the argon in the sputtering atmosphere is greater than approximately 25%.

4. The method of claim 3, wherein the ratio is greater than approximately 50%.

5. The method of claim 4, wherein the ratio is approximately 75%.

6. The method of claim 1, wherein:
a sputtering target power is between approximately 80 watts and approximately 300 watts; and
a total sputtering pressure is between approximately 9 millitorr and approximately 20 millitorr.

7. The method of claim 6, wherein the sputtering pressure is approximately 15 millitorr.

8. The method of claim 6, wherein the sputtering target power is approximately 100 watts.

9. The method of claim 1, further comprising applying over the roughened surface of the substrate an interposing layer comprising a material enhancing adhesion of the iridium oxide film to the substrate.

10. The method of claim 9, wherein the material is selected from the group consisting of: titanium, iridium, niobium and zirconium.

11. An implantable medical electrode comprising a substrate and an iridium oxide surface, the surface formed by applying a film of iridium oxide over a roughened surface of the substrate using direct current magnetron sputtering in which a sputtering atmosphere comprises oxygen and argon, and wherein the film has a microstructure exhibiting a columnar growth pattern.

12. The electrode of claim 11, wherein the substrate comprises a platinum iridium alloy.

13. The electrode of claim 11, wherein the substrate comprises titanium.

14. The electrode of claim 11, wherein a ratio of the oxygen to the argon in the sputtering atmosphere is greater than approximately 25%.

15. The electrode of claim 14, wherein the ratio is greater than approximately 50%.

16. The electrode of claim 15, wherein the ratio is approximately 75%.

17. The electrode of claim 11, wherein the roughened surface of the substrate comprises a material layer extending between the substrate and the iridium oxide film, the material layer comprising a material enhancing adhesion of the iridium oxide film to the substrate.

18. The electrode of claim 17, wherein the material is selected from the group consisting of titanium, iridium, niobium and zirconium.

19. The electrode of claim 11, wherein a sputtering target power is between approximately 80 watts and approximately 300 watts, and a total sputtering pressure is between approximately 9 millitorr and approximately 20 millitorr.

20. The electrode of claim 19, wherein the sputtering pressure is approximately millitorr.

21. The electrode of claim 19, wherein the sputtering target power is approximately 100 watts.

22. The electrode of claim 11, wherein a sputtering deposition rate is between approximately 100 angstroms/minute and approximately 2500 angstroms/minute.

23. An implantable medical electrode, comprising:
a substrate including a mechanically roughened surface; and
a direct current magnetron sputtered iridium oxide film extending over the surface, the film having a thickness greater than or equal to approximately 15,000 angstroms and a microstructure exhibiting a columnar growth pattern.

24. The electrode of claim 23, wherein the thickness of the film is greater than approximately 20,000 angstroms.

25. The electrode of claim 23, wherein the roughened surface of the substrate comprises a material layer extending between the substrate and the iridium oxide film, the material layer comprising a material enhancing adhesion of the iridium oxide film to the substrate.

26. The electrode of claim 25, wherein the material is selected from the group consisting of: titanium, iridium, niobium and zirconium.

27. The electrode of claim 25, wherein the thickness of the iridium oxide film is greater than or equal to approximately 20,000 angstroms.

* * * * *